United States Patent
Hartford

(12) United States Patent     (10) Patent No.: US 7,066,341 B1
Hartford     (45) Date of Patent: Jun. 27, 2006

(54) PIVOTAL INSTRUMENT HOLDER

(76) Inventor: Scott M. Hartford, 8 Matchett Industrial Park Dr., Pierceton, IN (US) 46562

( * ) Notice: Subject to any disclaimer, the term of this patent is extended or adjusted under 35 U.S.C. 154(b) by 123 days.

(21) Appl. No.: 10/462,115

(22) Filed: Jun. 13, 2003

(51) Int. Cl.
*A47F 7/00* (2006.01)

(52) U.S. Cl. .................................... 211/85.13; 211/169

(58) Field of Classification Search ............. 211/85.13, 211/169, 169.1, 126.1, 131.1, 131.2, 133.6, 211/88.01, 82, 90.02, 81, 70.6, 168; 206/305, 206/373, 438, 363, 370; 422/300, 297; 248/659, 248/500

See application file for complete search history.

(56) References Cited

U.S. PATENT DOCUMENTS

| | | | | |
|---|---|---|---|---|
| 812,343 | A * | 2/1906 | Horner | 312/270.2 |
| 2,047,097 | A * | 7/1936 | Dunbar | 211/169.1 |
| 2,408,227 | A * | 9/1946 | Ramsey | 206/379 |
| 3,074,539 | A * | 1/1963 | Rogovin | 206/379 |
| 3,259,748 | A * | 7/1966 | Lammers | 250/507.1 |
| 4,064,992 | A * | 12/1977 | Ralston et al. | 211/75 |
| 4,342,391 | A * | 8/1982 | Schainholz | 206/370 |
| 4,669,617 | A * | 6/1987 | Boeckmann et al. | 211/69.7 |
| 5,215,726 | A * | 6/1993 | Kudla et al. | 422/297 |
| 5,449,069 | A * | 9/1995 | Pijanowski et al. | 206/370 |
| 5,927,493 | A * | 7/1999 | Colombo | 206/372 |
| 6,360,892 | B1 * | 3/2002 | Chen | 206/376 |
| 6,439,401 | B1 * | 8/2002 | Battaglia et al. | 211/59.2 |

* cited by examiner

*Primary Examiner*—Jennifer E. Novosad
(74) *Attorney, Agent, or Firm*—Botkin & Hall, LLP

(57) ABSTRACT

An instrument holder usable in a tray for holding surgical instruments includes a housing that pivots about an axis between a closed position adjacent the floor of the tray and an open position angularly spaced from the tray floor. The holder may include a releasable locking mechanism to prevent the holder from shifting from its open position.

6 Claims, 8 Drawing Sheets

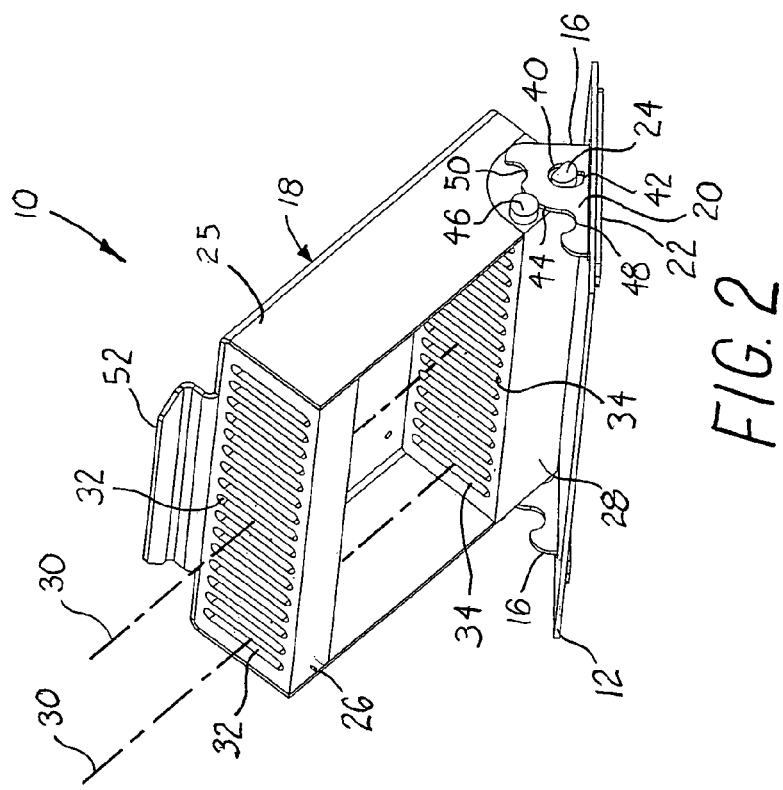
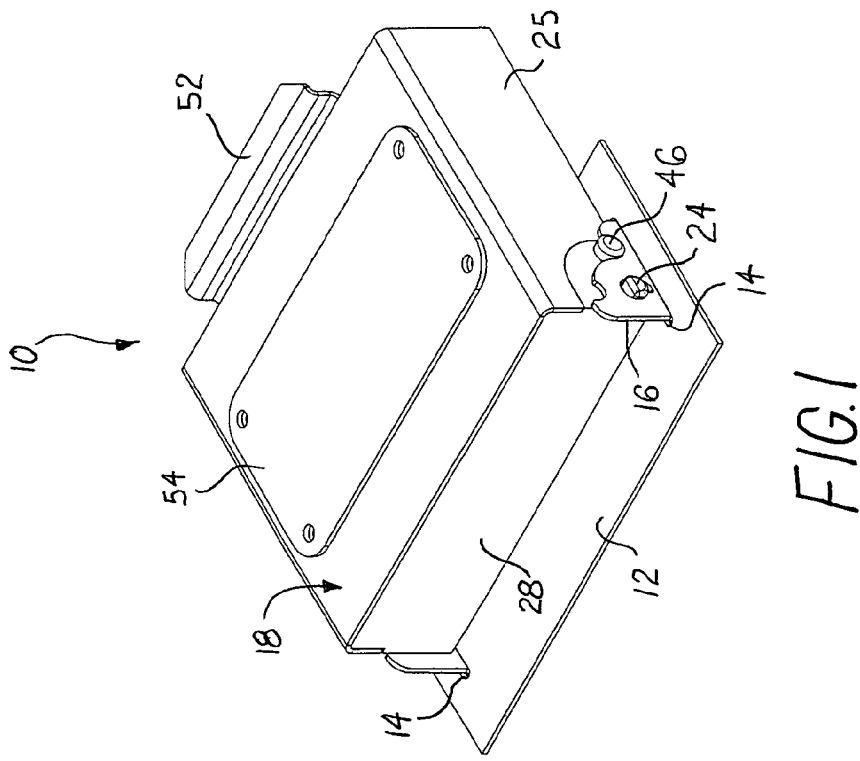

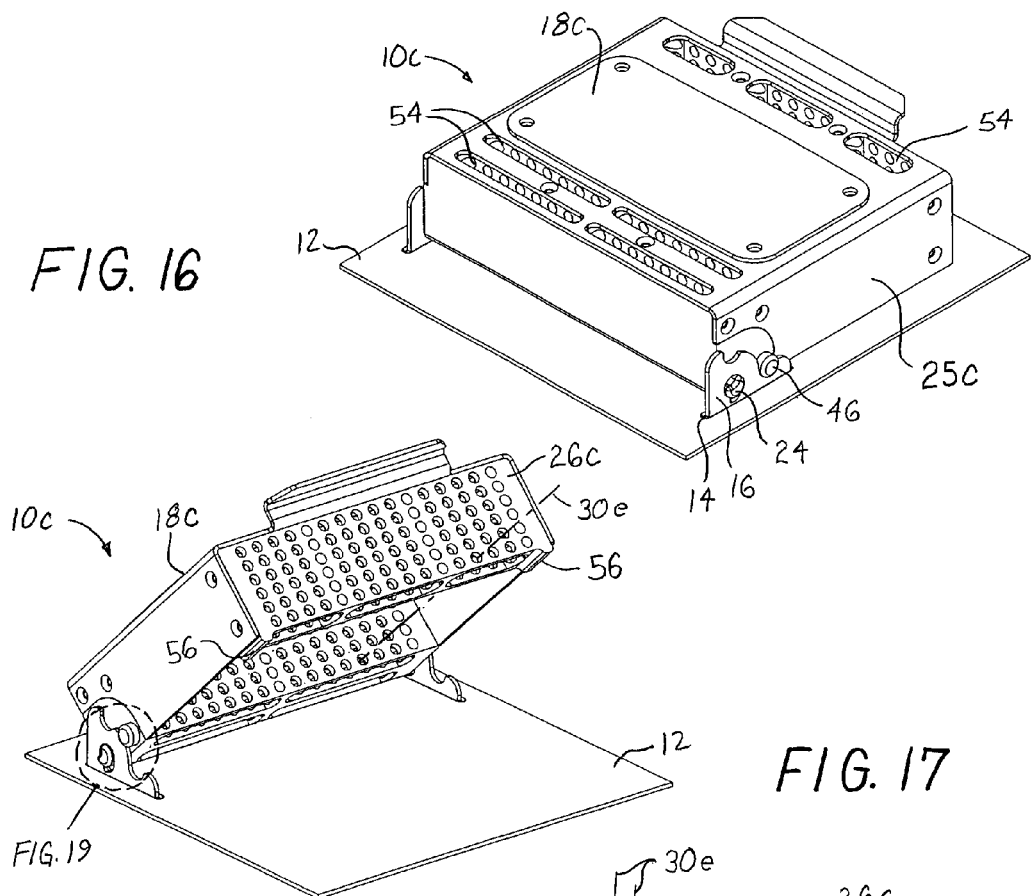
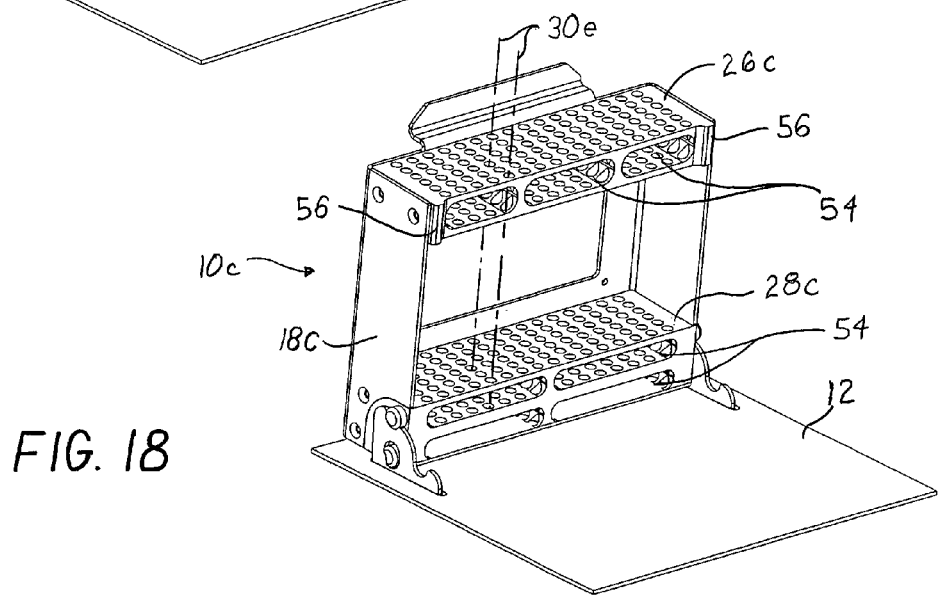

PIVOTAL INSTRUMENT HOLDER

FIELD OF THE INVENTION

The invention disclosed herein relates to a tray for holding medical instruments such as surgical tools.

BACKGROUND OF THE INVENTION

Medical instruments such as surgical tools should be sterile when used in order to reduce unwanted infections. These sterilized instruments need to be readily accessible and within easy reach of the user when it is desired to use them.

SUMMARY OF THE INVENTION

The invention disclosed herein provides a holder for medical instrumentation. The holder includes a housing for the instrumentation that is pivotally shiftable about a pair of trunnions, which engage a pair of brackets attached to the floor of a tray. The housing may be pivotally shifted about the trunnions between a closed horizontal storage position generally adjacent the floor of the tray and an open vertical position in which the instruments are accessible for use. The trunnions and brackets cooperate with each other to releasably secure the housing in its open position.

An object of the invention is to provide a holder for medical instrumentation which will provide easy access to sterilized instruments when needed.

BRIEF DESCRIPTION OF THE DRAWINGS

These and other aspects of the invention will be apparent from the following description, with reference to the accompanying drawings, in which:

FIG. 1 shows an instrument holder of this invention in its closed position;

FIG. 2 shows the instrument holder of FIG. 1 in a partially open position;

FIG. 16 shows a fourth embodiment of the instrument holder in its closed position FIG. 17 shows the instrument holder of FIG. 16 in a partially open position;

FIG. 18 shows the instrument holder of FIG. 16 in its open position; and,

DETAILED DESCRIPTION

Figure 3:
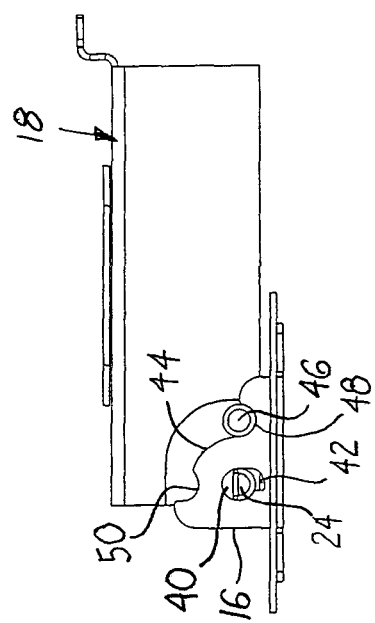
FIG. 3 is a side view of the instrument holder of FIG. 1.
Figure 4:
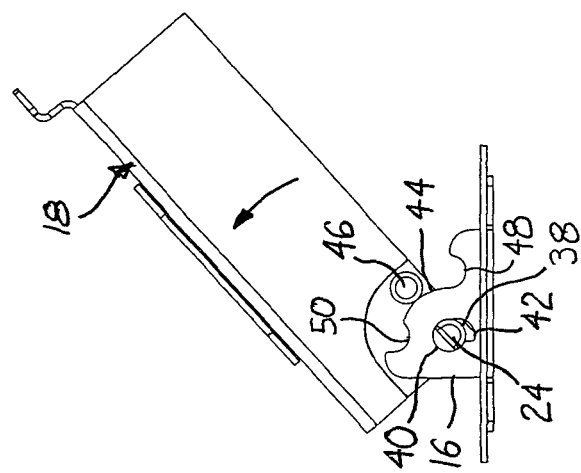
FIG. 4 is a side view of the partially open instrument holder of FIG. 2.

Referring now to the drawings, an instrument holder 10 as depicted in FIGS. 1–5 is used to carry medical instruments such as surgical tools. Instrument holder 10 is carried within a tray having a floor 12. A pair of brackets 16 is provided for supporting a housing 18 which will carry the instrumentation. Each bracket 16 includes a wall 20 fitted upwardly through an opening 14 in floor 12 and a base 22 abutting and attached to the underside of tray floor 12. Housing 18 is pivotally shiftable about a pair of trunnions 24 between a closed horizontal storage position adjacent to tray floor 12 (shown in FIG. 3) and an open use position relative to the tray floor (shown in FIG. 5). The open position of housing 18 is preferably approximately perpendicular to tray floor 12. The closed position of housing 18 is preferably approximately parallel to tray floor 12.

Housing 18 includes a generally box shaped frame 25 of sheet metal which supports two retention blocks 26, 28. Front instrument retention block 26 spans the front open end of frame 25, and rear instrument retention block 28 spans the rear open end of the frame. Retention blocks 26, 28 are preferably made of surgical grade machinable plastic, such as available under the trade name PROPYLUX™, or any other suitable machinable material. Retention blocks 26, 28 are spaced from each other and have a plurality of aligned instrument bores 30 for accepting various medical instrumentation (not shown). Instrument bores 30 are formed as through bores 32 in front retention block 26 and as closed ended or blind bores 34 in rear retention block 28. Instrument bores 30 are generally parallel to frame 25 such that an instrument may be inserted into an instrument bore from the exterior side of front retention block 26 through a through bore 32 and into an aligned blind bore 34 in rear retention block 28. The blind bore 34 prevents the instrument from falling out of instrument bore 30 when housing 18 is in its open position.

Trunnions 24 protruding from opposite sides of rear retention block 28 extend beyond frame 25. In cross section, trunnions 24 are approximately semi-circular with a flat face 36 opposite the curved portion 38. Trunnions 24 are fitted into corresponding openings 40 in bracket walls 20. Each opening 40 is circular and provides a complementary journalled fit for the inserted trunnions 24 except for a slot 42 oriented perpendicular to floor 12 and having a cross sectional shape corresponding to the cross section of the trunnions. Each slot 42 extends downwardly from the bottom of each bracket hole 40 and accepts its trunnion 24 in an interference fit only when the trunnion's flat portion 36 is aligned with the corresponding flat portion of the slot.

A cam surface 44 is provided along each bracket wall 20 arcuately extending between a lower cradle 48 and an upper recessed cradle 50. Cam followers 46 protrude outwardly from opposite sides of rear retention block 28 forwardly spaced from trunnions 24. Cam followers 46 follow cam surface 44 when housing 18 is rotated about trunnions 24, as described more particularly herein below. Cam follower 46 is preferably spaced from cam surface 44 in the lower portions of its travel between the open and closed positions to reduce frictional resistance of the pivot mechanism. Alternatively, cam followers 46 may slide along the entire cam surfaces 44 between lower cradle 48 when housing 18 is in its closed position and upper cradle 50 when the housing is in its open position. When housing 18 is in its closed position, cam followers 46 rest in lower cradles 48 and trunnions 24 are urged upwardly in opening 40 against bracket wall 20, thereby supporting the cantilevered housing.

Figure 5:
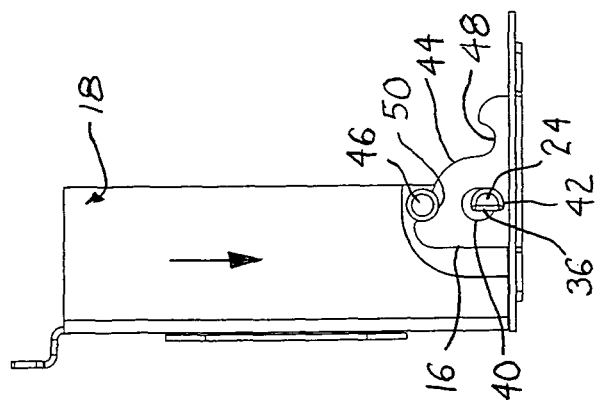
FIG. 5 is a side view of the instrument holder of FIG. 1 in its open position.
Figure 7:
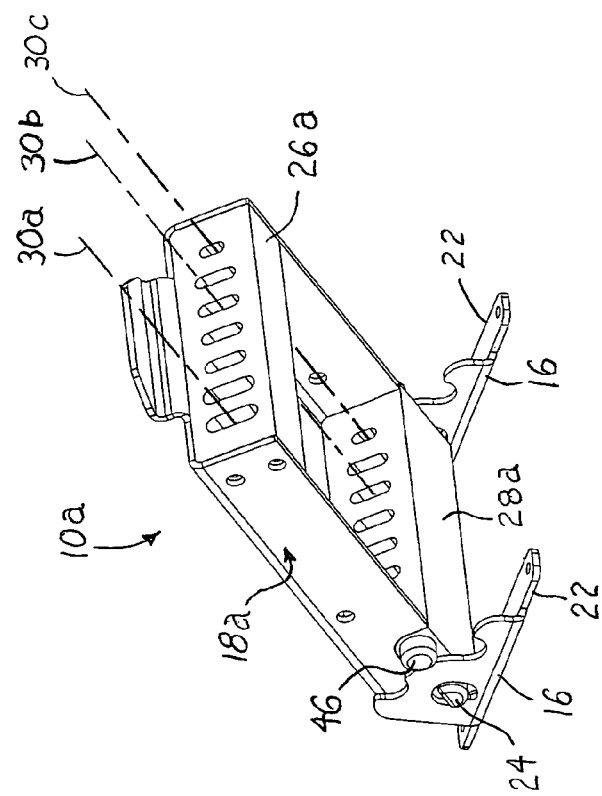
FIG. 7 shows the instrument holder of FIG. 6 in a partially open position.
Figure 6:
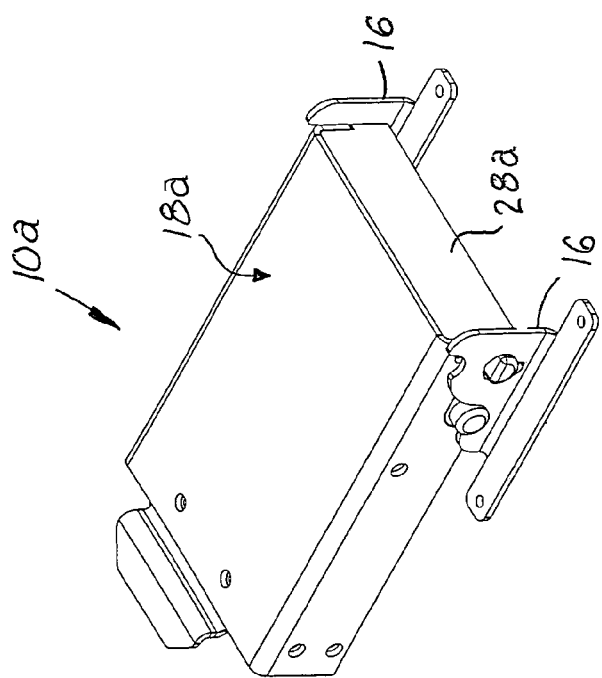
FIG. 6 shows a second embodiment of the instrument holder in its closed position.
Figure 10:
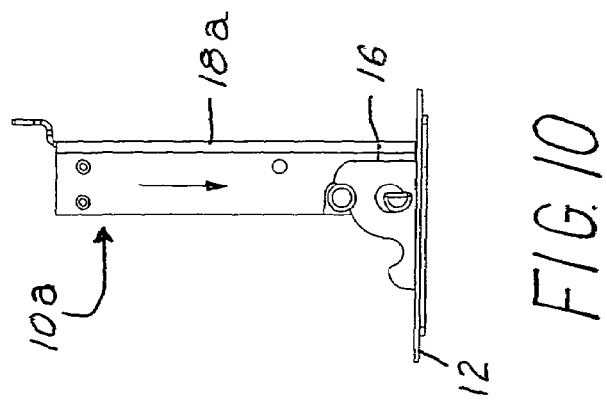
FIG. 10 is a side view of the instrument holder of FIG. 6 in its open position.
Figure 9:
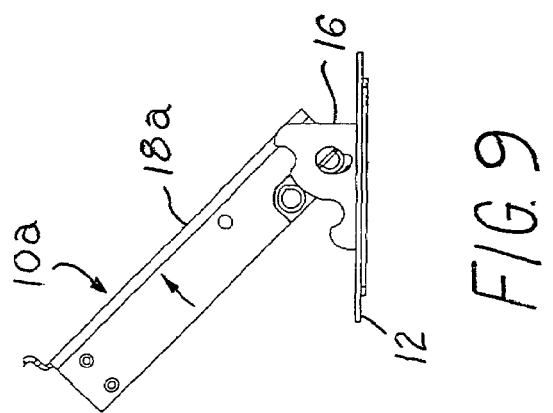
FIG. 9 is a side view of the partially open instrument holder of FIG. 7.
Figure 8:
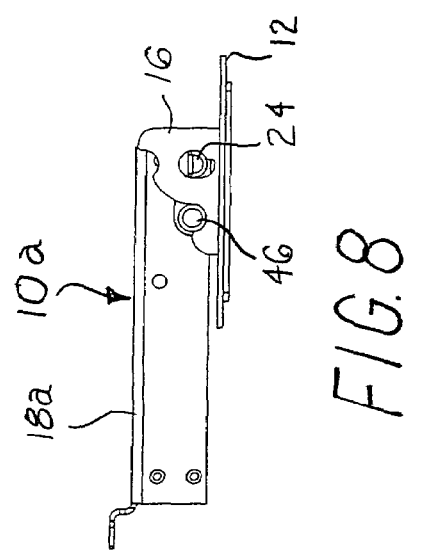
FIG. 8 is a side view of the closed instrument holder of FIG. 6.
Figure 12:
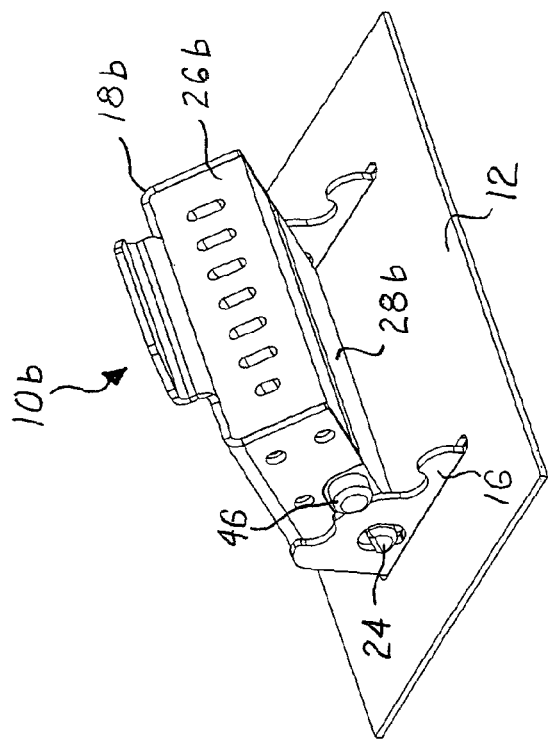
FIG. 12 shows the instrument holder of FIG. 11 in a partially open position.
Figure 11:
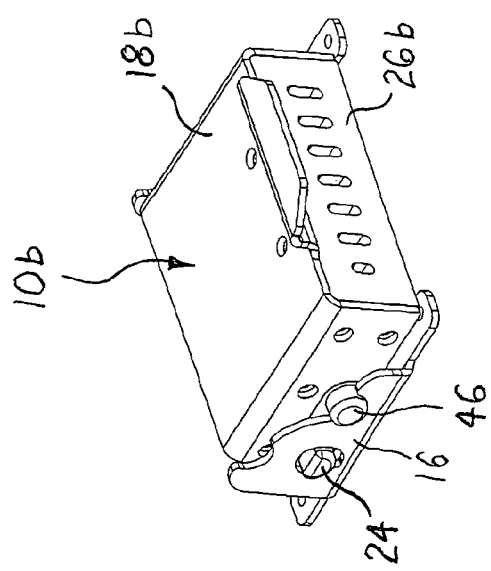
FIG. 11 shows a third embodiment of the instrument holder in its closed position.
Figure 15:
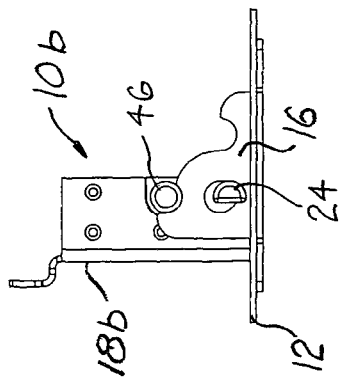
FIG. 15 is a side view of the instrument holder of FIG. 11 in its open position.
Figure 14:
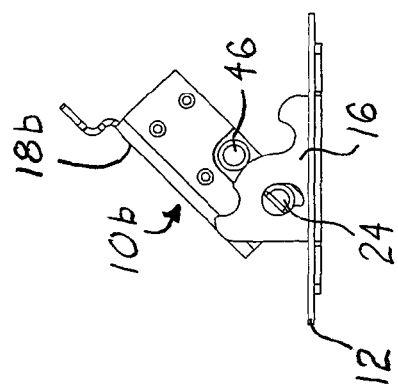
FIG. 14 is a side view of the partially open instrument holder of FIG. 12.
Figure 13:
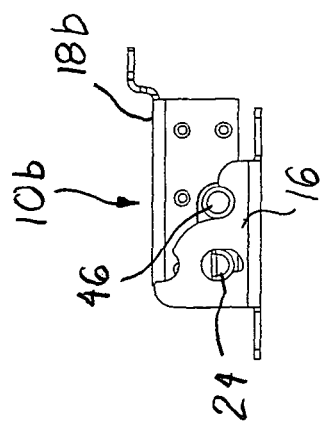
FIG. 13 is a side view of the closed instrument holder of FIG. 11.

When housing 18 is in its open position, cam followers 46 rest in upper cradles 50, which are recessed in relation to cam surfaces 44. Upper cradles 50 are radially aligned above slots 42, allowing the cam followers to shift downwardly from cam surface 44, which thereby allows trunnions 24 to shift downwardly into slots 42 when housing 18 is in its open position. Upper cradles 50 also prevent housing 18 from shifting beyond its open position by obstructing cam follower 46. When cam followers 46 are resting within recessed cradles 50 and trunnions 24 are fitted within slots 42, housing 18 is maintained in its open position with the exterior side of rear retention block 28 preferably resting on tray floor 12 as shown in FIG. 5 by the interference fit of the cam followers within the upper cradles and the flat faced trunnions 24 within the slots 42. In practice, the tray will usually be placed on a horizontal surface such that gravity will urge housing 18, cam followers 46, and trunnions 24 downwardly into slots 42 and recessed saddle 50 when in its vertical open position.

To open housing 18, a user grips a handle 52, which protrudes outwardly from the front end of the housing, and tilts or pivots the housing upwardly about trunnions 24. When cam followers 46 reach recessed upper cradles 50, housing shifts downwardly such that the cam followers rest within the upper cradles and flat faced trunnions 24 are fitted into slots 42. To close housing 18, a user grips handle 52 and urges the housing in the reverse direction, or forwardly, tilting the housing downwardly about trunnions 24. The user is not required to independently lift trunnions 24 out of slots 42, but only needs to urge housing 18 horizontally. Cam surface 44 urges cam followers 46 upwardly out of recessed upper cradles 50, which lifts trunnions 24 out of slots 42 in holes 40, thereby allowing the housing to rotate freely about the trunnions. Housing 18 is then pivoted toward its closed position about trunnions 24 until cam followers 46 are again resting within lower cradles 42.

A decorative plate—or name plate—54 on the exterior side of housing 18 may be used for instructional, informational, or decorative inscriptions and the like. A pair of instrument holders 10 may be opposingly fitted into a tray with their front ends facing each other.

To use instrument holder 10, instruments are inserted into aligned instrument bores 30 when the housing is in its open position. Housing 18 is then shifted to its closed position and the entire tray and instrument holder 10 may be sterilized. When it is desired to use the instruments, the tray is placed near the area of use, and housing 18 is shifted to its open position and locked as hereinbefore described. A user may then selectively remove instruments from instrument bores 30 as needed.

An alternative embodiment of instrument holder 10a is depicted in FIGS. 6–10 with similar structures having the same numbers as hereinbefore assigned. In this embodiment, different sized instrument bores 30a, 30b, 30c in front and rear retention blocks 26a, 28a accommodate different sized instruments.

Another alternative embodiment of instrument holder 10b is depicted in FIGS. 11–15 with similar structures having the same numbers as hereinbefore assigned. In this embodiment, a shorter housing 18b provides less space between front and rear retention blocks 26b, 28b. Alternatively, a single retention block spanning the entire length of bores 30d could be used instead of separate front and rear retention blocks 26b, 28b. Instrument holder 10b could be used to hold shorter instruments.

A further alternative embodiment of instrument holder 10c is depicted in FIGS. 16–18 with similar structures assigned the same numbers as before. In this embodiment, steam holes 54 are located in frame 25c and through retention blocks 26c, 28c. Smaller, circular bores 30e are regularly spaced in rows and columns for holding instruments. Feet 56 protruding downwardly from opposite ends of the front retention block 26c rest on tray floor 12 when housing 18c is in its closed position. Feet 56 may thereby be used to support housing 18 when closed such that housing is not cantilevered from trunnions 24 and cam followers 46 in the closed position. Steam holes 54 allow the passage of steam through housing 18 for sterilization.

Figure 19A:
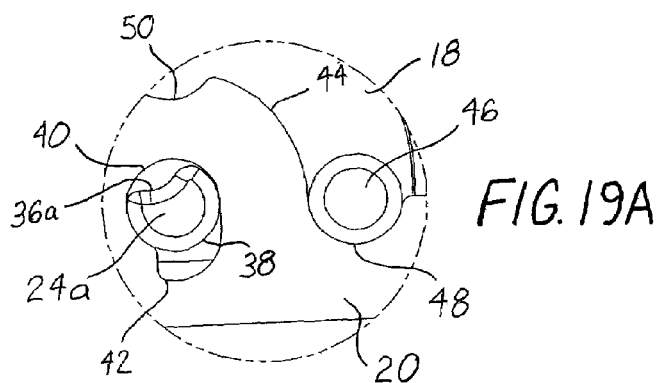
FIGS. 19A–19E are detailed views of the pivot mechanism in successive positions between its closed position in FIG. 19A and its open position in FIG. 19E.
Figure 19B:
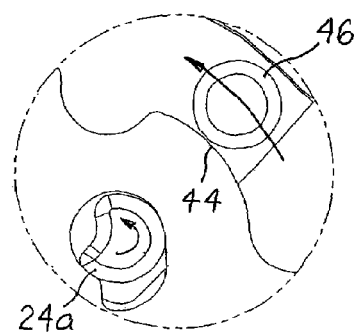
Figure 19C:
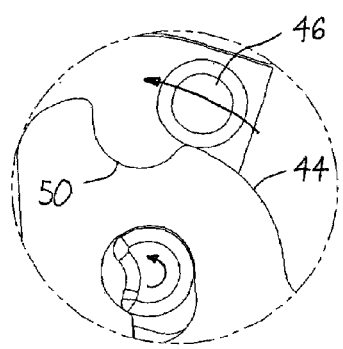
Figure 19D:
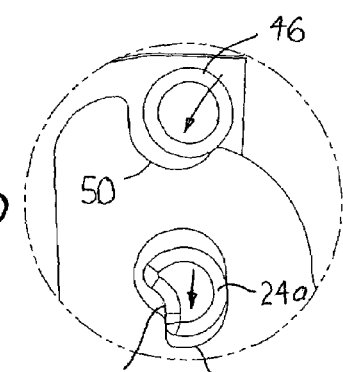
Figure 19E:
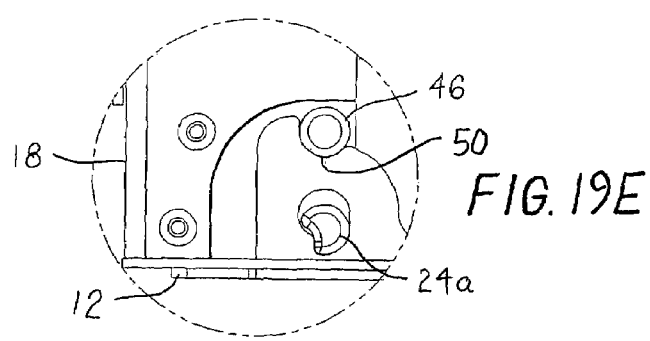

FIGS. 19A–19E show the preferred embodiment of the pivot mechanism shown on instrument holder 10c in successive positions between closed and open positions. In FIG. 19A, the housing is in its closed position with cam follower 46 resting in lower cradle 48. A trunnion 24a is carried within circular opening 40 in bracket wall 20. A slot 42 extends downwardly from a lower portion of opening 40 in alignment with upper recessed cradle 50. Trunnion 24a has a generally semi-circular cross-section that fits snuggly within circular opening 40. Trunnion 24a includes a curved cut-away portion 36a opposite a circular portion 38. Cut-away portion 36a of trunnion 24a allows the trunnion to slide into slot 42 only when the housing is in its open position, as shown in FIG. 19E.

As the housing is shifted upwardly around trunnion 24a, cam follower 46 is spaced from cam surface 44 in the lower portion of the cam follower's travel, as depicted in FIG. 19B. As cam follower 46 nears upper portion of its travel, as shown in FIG. 19C, the cam follower re-engages with cam surface 44 before reaching upper recessed cradle 50. As cam follower 46 travels into upper cradle 50, shown in FIG. 19D, cut-away portion 36a of trunnion 24a aligns with slot 42 to allow the trunnion to slide into the slot as the cam follower slides into the upper recessed cradle. When the housing is completely open as depicted in FIG. 19E, the back of housing 18 rests fully on tray floor 12, trunnion 24a is fitted into slot 42, and cam follower 46 is carried within upper cradle 50. To close, the housing is urged horizontally in the reverse direction, thereby causing cam follower 46 to raise trunnion 24a out of slot 42 as it shifts out of upper cradle 50. A slight space between trunnion 24a and slot 42 allows the trunnion to rotate slightly as cam follower 46 shifts out of upper cradle 50. The housing may then be closed through reverse succession of the steps hereinbefore described.

The detailed description related herein is meant only to exemplify the invention to enable those skilled in the art to make and use it. It is not intended to be a limitation from other minor and obvious variations on the embodiments described, all of which variations are expressly included herein

We claim:

1. A pivotal instrument holder used in combination with a tray having a floor, said holder comprising:
   a pair of brackets attached to said tray floor;
   a housing for accepting instrumentation;
   a pair of axially aligned trunnions carried by said housing engaging said brackets, said housing pivotally shiftable about said trunnions between a horizontal closed position and a vertical open position, said trunnions and brackets cooperating with one another to releasably secure said housing in its open position;
wherein said trunnions are fitted into openings in each of said brackets, each said opening having a slotted portion narrower than the width of said opening, each trunnion slidably fitting downwardly into said slotted portion as said housing shifts into its said open position.

2. The instrument holder of claim 1 and further comprising:
   a cam carried by one of said brackets; and,
   a cam follower carried by said housing adjacent said cam, the cam follower traveling along the cam for guiding said housing as the housing shifts between its said open and closed positions.

3. The instrument holder of claim 1 wherein said housing includes a bore for accepting said instrumentation.

4. The instrument holder of claim 1 wherein said housing includes at least one pair of aligned bores axially spaced from each other for accepting said instrumentation.

5. The instrumentation holder of claim 4 wherein one of said aligned bores is a through bore and the other of said aligned bores is a closed ended bore, said instrumentation being insertable through said through bore and into said closed ended bore when said housing is in its open position.

6. A pivotal instrument holder used in combination with a tray having a floor, said holder comprising:
   a pair of brackets attached to said tray floor;
   a housing for accepting instrumentation;
   a pair of axially aligned trunnions carried by said housing engaging said brackets, said housing pivotally shiftable about said trunnions between a horizontal closed position and a vertical open position, said trunnions and brackets cooperating with one another to releasably secure said housing in its open position, wherein said trunnions are fitted into openings in each of said brackets, each said opening having a narrow slotted portion, each trunnion slidably fitting downwardly into said slotted portion when said housing is in its said open position, a cam carried by one of said brackets; and,
   a cam follower carried by said housing adjacent said cam, the cam follower traveling along the cam for guiding said housing as the housing shifts between its said open and closed positions, said cam including a recess aligned with said slotted portion of said openings, said trunnions and said cam follower slidably received within said respective slotted portions and said recess when said holder is in its said open position.

* * * * *